United States Patent [19]
Tomes et al.

[11] Patent Number: 5,921,477
[45] Date of Patent: *Jul. 13, 1999

[54] APPARATUS FOR TISSUE PREPARATION

[75] Inventors: Dwight T. Tomes, Cumming; John G. K. Williams; Michael E. Moore, both of Ankeny, all of Iowa

[73] Assignee: Pioneer Hi-Bred International, Inc., Johnston, Iowa

[*] Notice: This patent issued on a continued prosecution application filed under 37 CFR 1.53(d), and is subject to the twenty year patent term provisions of 35 U.S.C. 154(a)(2).

[21] Appl. No.: 08/713,507

[22] Filed: Sep. 13, 1996

[51] Int. Cl.$^6$ .................................................. B02C 19/12
[52] U.S. Cl. ..................... 241/2; 211/74; 241/36; 241/170; 241/184; 366/212; 422/104
[58] Field of Search .................... 241/2, 36, 170, 241/179, 283, 199.1, 184; 435/307, 306.1, 307.1; 366/111, 112, 114, 208, 212; 211/74; 422/104

[56] References Cited

U.S. PATENT DOCUMENTS

| | | | |
|---|---|---|---|
| 3,310,292 | 3/1967 | Moore | 366/111 |
| 3,556,731 | 1/1971 | Martin . | |
| 3,736,614 | 6/1973 | Crostic et al. . | |
| 3,789,670 | 2/1974 | Rosenwald . | |
| 4,043,514 | 8/1977 | Peterson | 241/36 |
| 4,118,801 | 10/1978 | Kraft et al. | 366/111 |
| 4,295,613 | 10/1981 | Moore et al. | 241/2 |
| 4,413,059 | 11/1983 | Tihon et al. | 241/283 |
| 4,534,858 | 8/1985 | Aldrich et al. . | |
| 4,556,639 | 12/1985 | Izawa et al. . | |
| 4,571,087 | 2/1986 | Ranney . | |
| 4,747,693 | 5/1988 | Kahl | 422/104 |
| 4,837,935 | 6/1989 | Maier et al. . | |
| 4,883,644 | 11/1989 | Perlman | 422/104 |
| 5,110,556 | 5/1992 | Lyman et al. . | |
| 5,114,858 | 5/1992 | Williams et al. . | |
| 5,153,136 | 10/1992 | Vandenburgh . | |
| 5,183,564 | 2/1993 | Hong . | |
| 5,272,092 | 12/1993 | Hamasaki et al. . | |
| 5,458,416 | 10/1995 | Edwards et al. | 366/212 |
| 5,464,773 | 11/1995 | Melendez et al. | 241/2 |
| 5,501,521 | 3/1996 | Hjalmarson | 366/208 |
| 5,707,861 | 1/1998 | Sherman et al. | 435/306.1 |

FOREIGN PATENT DOCUMENTS

296 15 162 U   12/1996   Germany .

*Primary Examiner*—Mark Rosenbaum
*Attorney, Agent, or Firm*—Zarley, Mckee, Thomte, Voorhees & Sease

[57] ABSTRACT

An apparatus and method for preparing tissue samples for DNA, RNA or protein extraction of the present invention includes a reciprocating saw mounted to a frame and connected to a plurality of tissue sample containers containing tissue samples and agitation members. By activating the reciprocating saw, the tissue samples are ground by the agitation members. A control circuit is connected to the saw for controlling the speed and duration of the agitation.

29 Claims, 9 Drawing Sheets

APPARATUS FOR TISSUE PREPARATION

BACKGROUND OF THE INVENTION

Field of the Invention

The present invention relates to tissue preparation. More particularly though not exclusively the present invention relates to an apparatus for preparing tissue for extracting material, such as proteins, nucleic acids, starches, carbohydrates, oils, and the like.

Problems in the Art

In scientific examination of plants and their cellular structures and components, it is often necessary to extract certain materials for close inspection, replication, experimentation, etc. These materials include nucleic acids, proteins, starches, carbohydrates, oils, and the like.

DNA, for example, is housed within the nucleus of a cell. Extraction of DNA is traditionally accomplished by rupturing the cell, thereby releasing the DNA for further extraction or purification. Cells can be ruptured by chemical or mechanical means. Larger tissue or cell samples are ground and then further treated to extract important components for study. A typical prior art apparatus for preparing tissue samples for DNA or protein extraction are arranged such that a plurality of containers are successively brought to a grinding or homogenization position and the contents agitated by an agitation bar or rod. One disadvantage of this design is the contamination of the reaction solutions that takes place due to the shared use of the same grinding bar. Also, only one sample can be homogenized at one time. Other prior art systems grind, agitate or disrupt samples various ways which are unsatisfactory. Such devices are typically expensive, complicated, and have undesirable results. There is a need for effective rapid grinding of multiple tissue samples. No prior art device has met this need.

Other prior art approaches are not as reliable, are not as easy to use, or cannot adequately perform the functions stated above. For example, one approach includes using a magnetic vibrating table to agitate the samples. However, magnetic vibrating tables have insufficient amplitude or stroke length that is needed to grind samples.

It can therefore be seen that there is a demand for a fast, simple, effective, and economic apparatus for preparing tissue samples for extraction of various materials.

Objects of the Invention

A general object of the present invention is the provision of an apparatus for tissue preparation which overcomes the deficiencies found in the prior art.

A further object of the present invention is the provision of an apparatus for tissue preparation which uses a reciprocating saw for grinding or agitating a number of tissue samples and preparing them for extraction.

A further object of the present invention is the provision of an apparatus for tissue preparation which reduces the complexity of extraction systems while increasing the simplicity and reliability of those systems and throughput.

Further objects, features, and advantages of the present invention include:

An apparatus for tissue preparation in which the user can easily control the speed and duration of the grinding.

An apparatus for tissue preparation which reduces the costs of extraction.

An apparatus for tissue preparation having various safety features to ensure the safety of a user.

These as well as other objects, features and advantages of the present invention will become apparent from the following specification and claims.

SUMMARY OF THE INVENTION

The present invention relates to an apparatus and method for preparing tissue samples for DNA material extraction. These materials include nucleic acids, proteins, carbohydrates, starches, oils, and the like. A reciprocating saw is mounted to a frame and is connected to a plurality of containers holding tissue samples. The tissue sample containers each hold one or more agitation members. When the reciprocating saw is activated, the plurality of containers agitate which causes the agitation members to grind the tissue samples in preparation for material extraction. The apparatus may optionally include a hingable cover for covering the plurality of containers while they are agitated. A control panel may be connected to the apparatus for controlling the operation of the reciprocating saw.

DETAILED DESCRIPTION OF THE PREFERRED EMBODIMENT

The present invention will be described as it applies to its preferred embodiment. It is not intended that the present invention be limited to the described embodiment. It is intended that the invention cover all alternatives, modifications, and equivalences which may be included within the spirit and scope of the invention.

Figure 1:
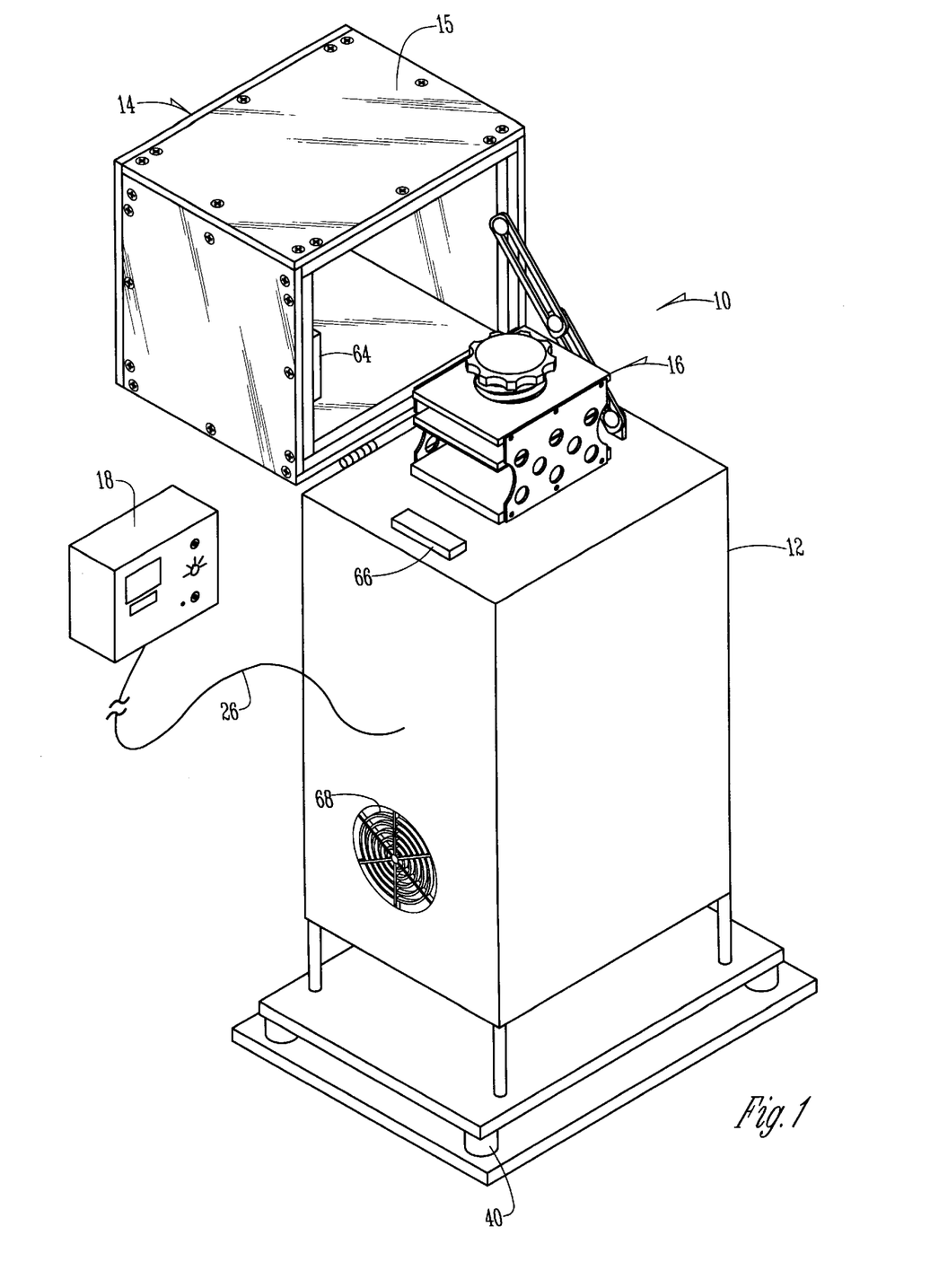
FIG. 1 is a perspective view of an embodiment of the present invention.
Figure 2:
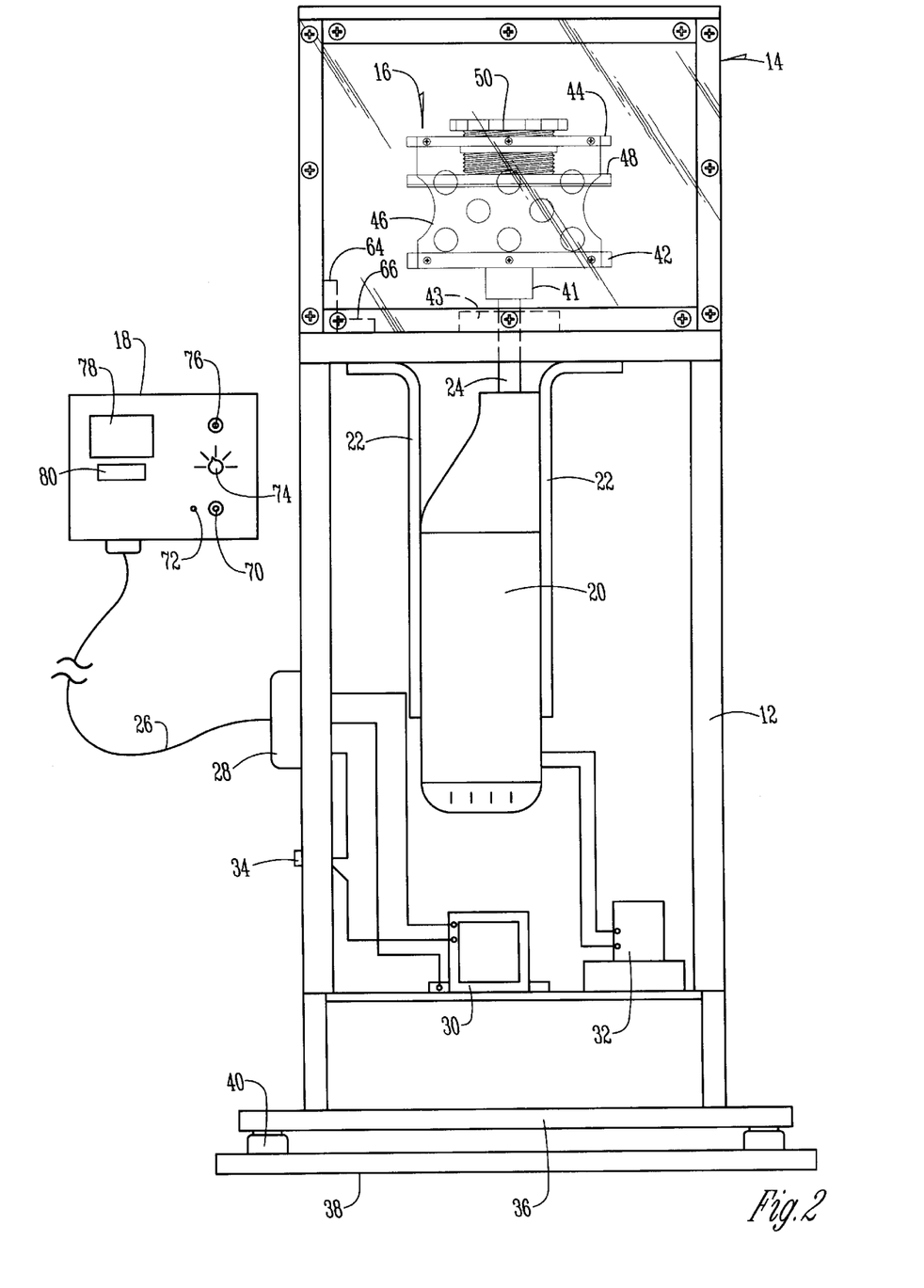
FIG. 2 is a front view showing the interior of the invention.

FIG. 1 shows an apparatus 10 for the preparation of tissue for material extraction. These materials include nucleic acids, proteins, starches, carbohydrates, oils, and the like. The apparatus 10 includes a housing 12 and a hinged cover 14 having sheets of polycarbonate 15 secured to it. The polycarbonate 15 used has the trade name LEXAN. The hinged cover 14 can be moved between an open position (FIG. 1) and a closed position (FIG. 2). Positioned above the housing 12 is a holder 16 used to hold tissue samples. When the hinged cover 14 is in the closed position, the hinged cover 14 encloses the holder 16. Connected to the apparatus 10 is a control panel 18 which is used to control the operation of the apparatus 10.

FIG. 2 shows the apparatus 10 with part of the housing 12 removed to show the interior of the housing 12. Disposed within the housing 12 is a reciprocating saw 20 mounted to the housing 12 by a pair of brackets 22. The preferred embodiment uses a commercial grade reciprocating saw, preferably manufactured by Milwaukee and known by the trade name "Sawzall". The reciprocating saw 20 includes a reciprocating member 24 which moves back and forth relative to the saw 20 when the saw 20 is activated. During the normal use of a saw such as reciprocating saw 20, the reciprocating member 24 would be coupled to a saw blade and used to cut various materials.

The control panel 18 is connected to a 9 pin CPC connector 28 mounted to the housing 12 by a cable 26. The connector 28 is electrically connected to the saw 20 and to other components within the housing 12. As shown in FIG. 2, connections are made to a 24 volt transformer 30 and a relay 32. In the preferred embodiment, transformer 30 is produced by Stancor, part number P-8575. The preferred relay 32 has a part number KRPA-11AG-24. Connected in line with one of the power lines is a 5 amp fuse 34. The operation of these electrical components are discussed below.

As shown in FIGS. 1 and 2, the housing 12 is mounted to a shock absorbing base comprised of a steel base 36, a wooden base 38, and rubber pads 40. The housing 12 is rigidly mounted to the steel base 36 which is mounted above the wooden base 38 by rubber pads 40. The rubber pads 40 absorb the shock caused by the operation of the reciprocating saw 20.

Figure 3:
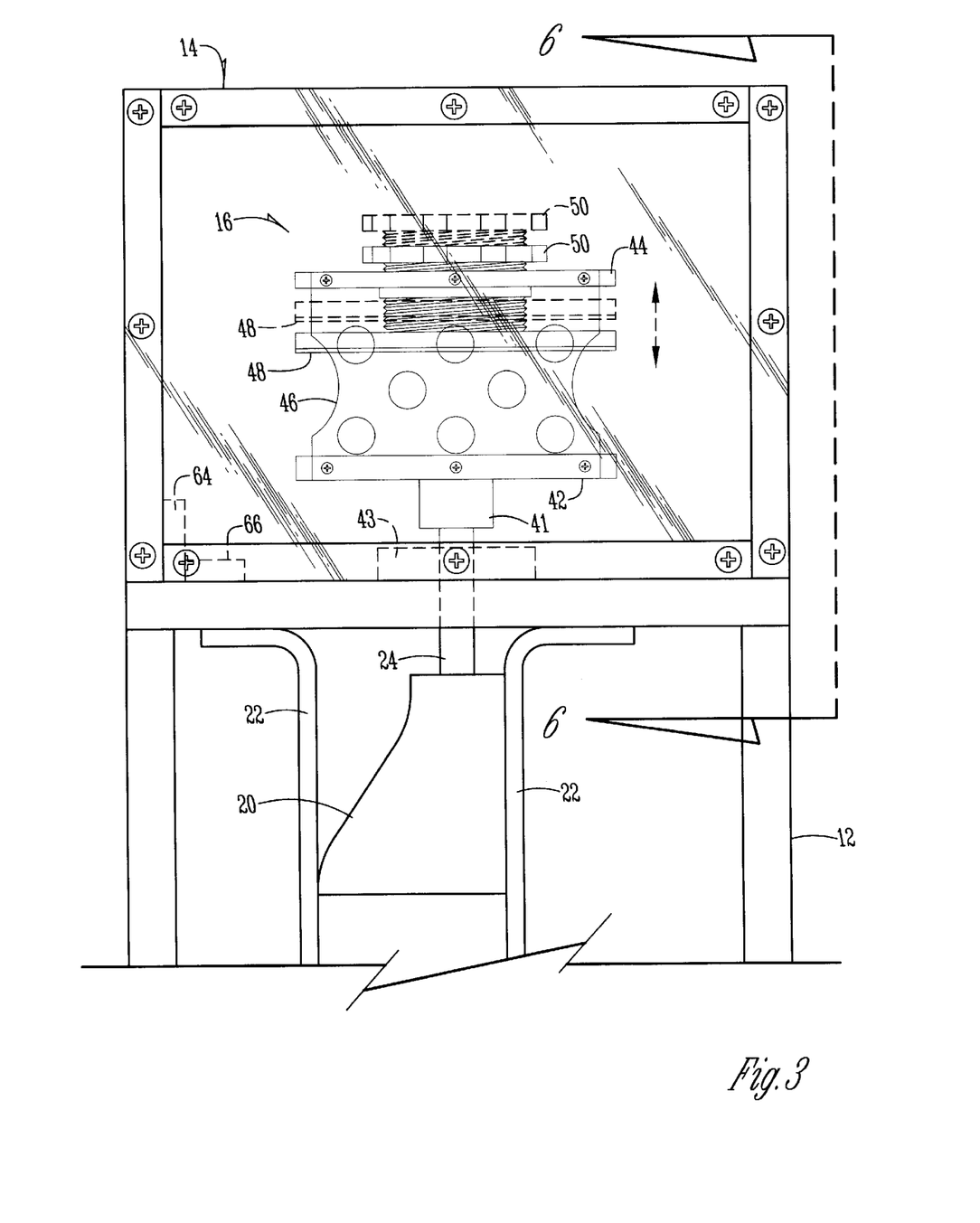
FIG. 3 is an enlarged partial view of the embodiment shown in FIG. 2.

FIG. 3 shows an enlarged view of the hinged cover 14 in the closed position and enclosing the holder 16. The holder 16 is coupled to the reciprocating member 24 by a cylindrical shaped coupler 41. When the saw 20 causes the reciprocating member 24 to agitate, the coupler 41 and holder 16 agitate with it. The reciprocating member 24 passes through a bushing 43 which is coupled to the housing 12. The guide 43 helps to stabilize the reciprocating member 24 and the holder 16.

The holder 16 consists of a lower tray 42 coupled to a top plate 44 by two sheets of polycarbonate 46. The sheets of polycarbonate sheets 46 are secured to the lower tray 42 and top plate 44 by a number of screws and hold the tray 42 and top plate 44 in a generally parallel position. Disposed between the lower tray 42 and the top plate 44 is an upper tray 48. The upper tray 48 is rotatably coupled to a threaded adjustment member 50 which is threadably engaged with the top plate 44. By rotating the adjustment member 50, the adjustment member 50 moves up or down relative to the top plate 44 moving with it the upper tray 48. In this way, the distance between the upper tray 48 and the lower tray 42 is controlled by rotating the adjustment member 50. FIG. 3 shows two extreme positions of the adjustment member 50 and the upper tray 48 in solid and dashed lines to illustrate the operation of these elements.

Figure 4:
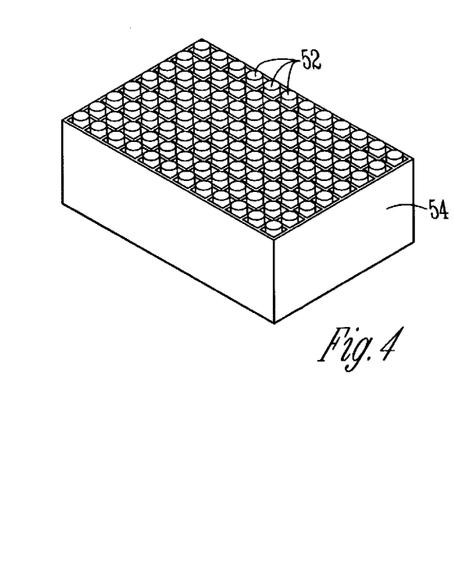
FIG. 4 is a view of a well plate holder and a plurality of well plates.
Figure 5:
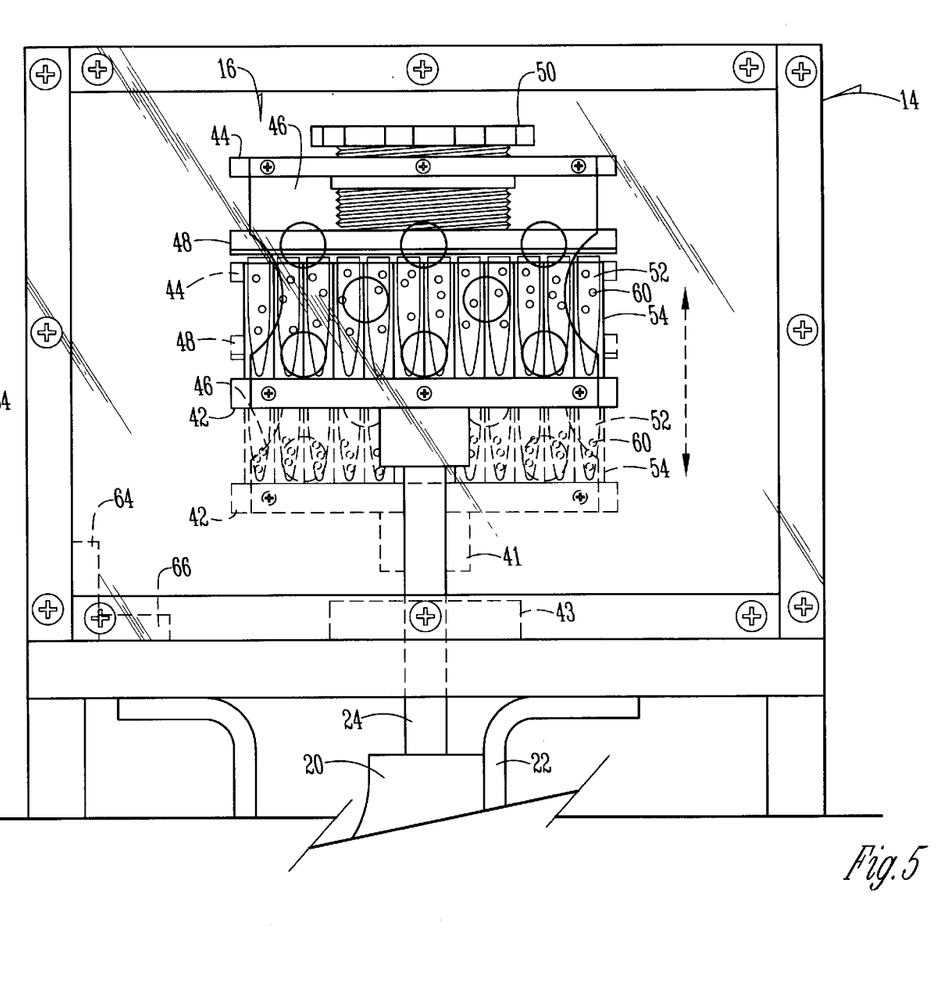
FIG. 5 is an enlarged front view showing the reciprocating motion of the holder.
Figure 6:
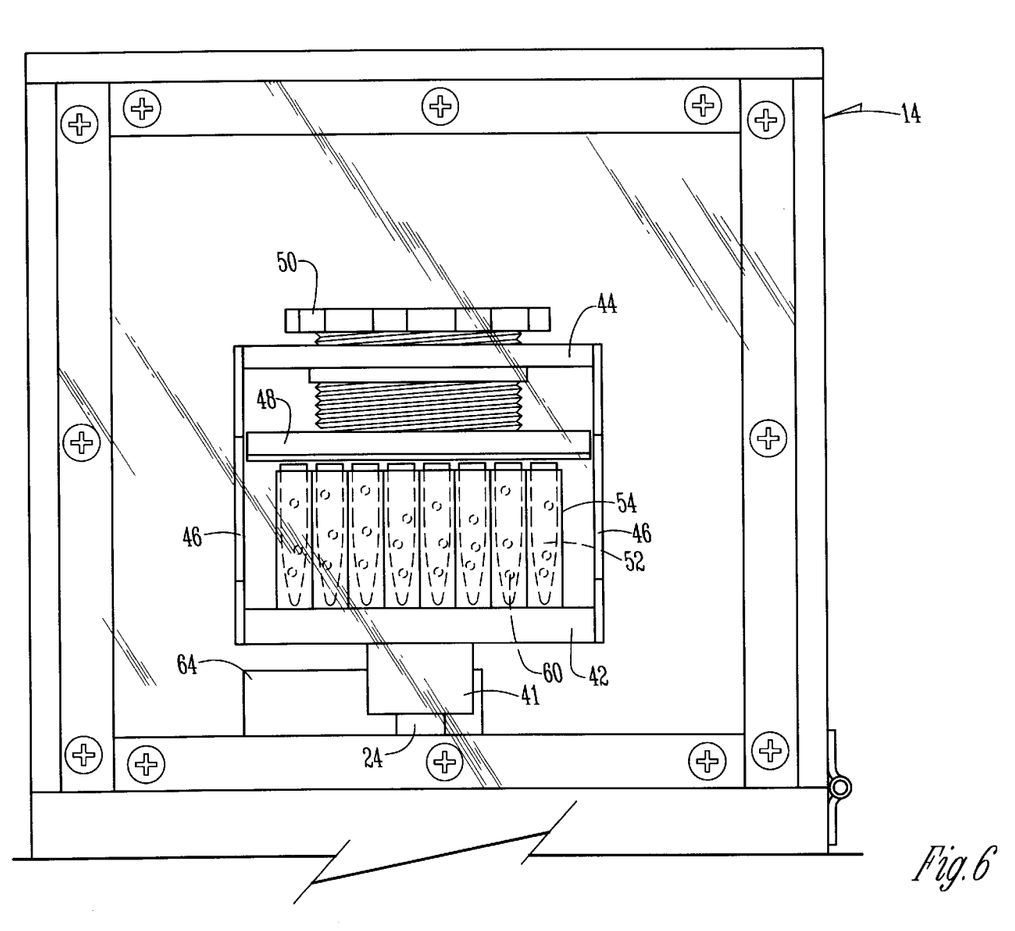
FIG. 6 is an enlarged partial side view of the invention taken along line 6—6 of FIG. 3.

FIG. 4 shows 96 tubes or wells 52 held by a well plate holder 54. The purpose of the tubes 52 is to hold samples from which protein and DNA are to be extracted. The well plate holder 54 can be inserted into the holder 16 as shown in FIGS. 5 and 6. The well plate holder 54 can be slid into the holder 16 between the lower tray 42 and upper tray 48. Once the well plate holder 54 and tubes 52 are inserted between the upper and lower trays 48 and 42, the adjustment member 50 can be rotated clockwise to secure the well plate holder 54 within the holder 16.

Figure 7:
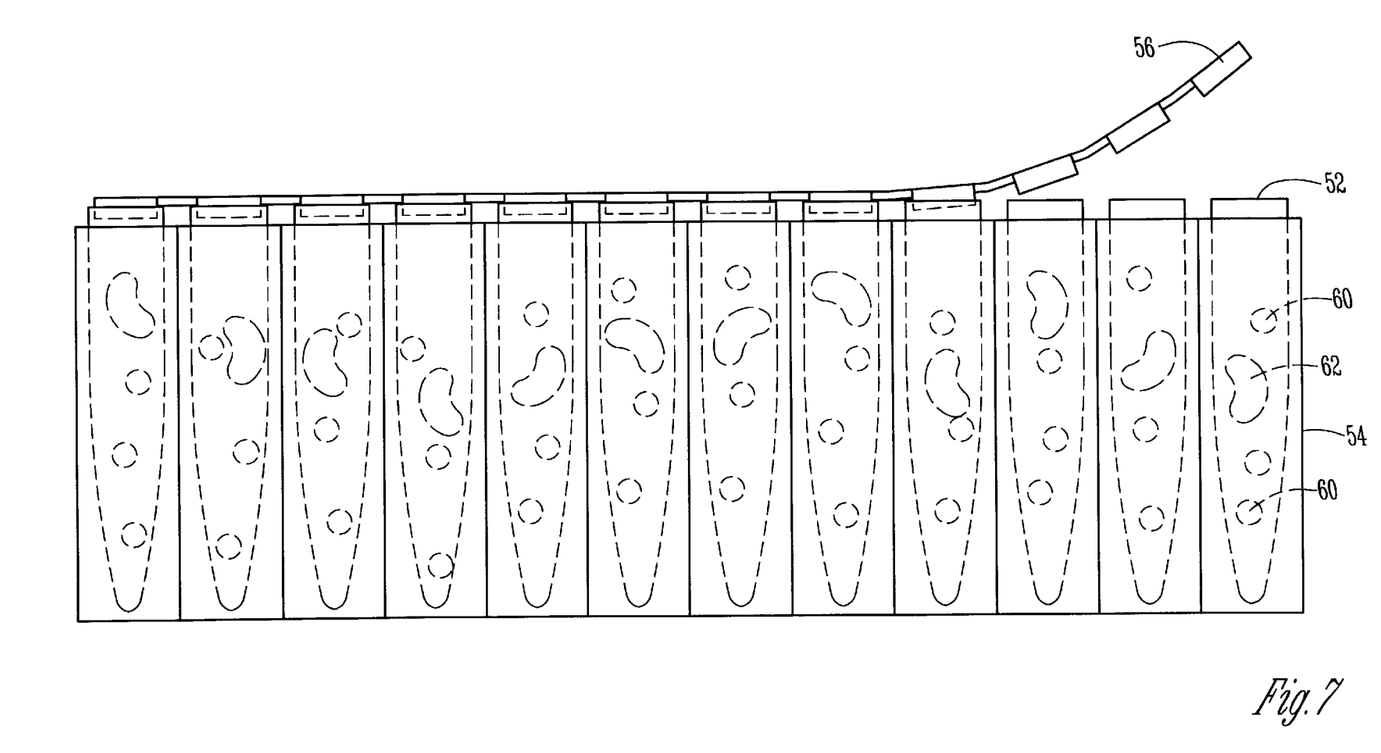
FIG. 7 is an enlarged side view of the well plate holder and the well plates.
Figure 8:
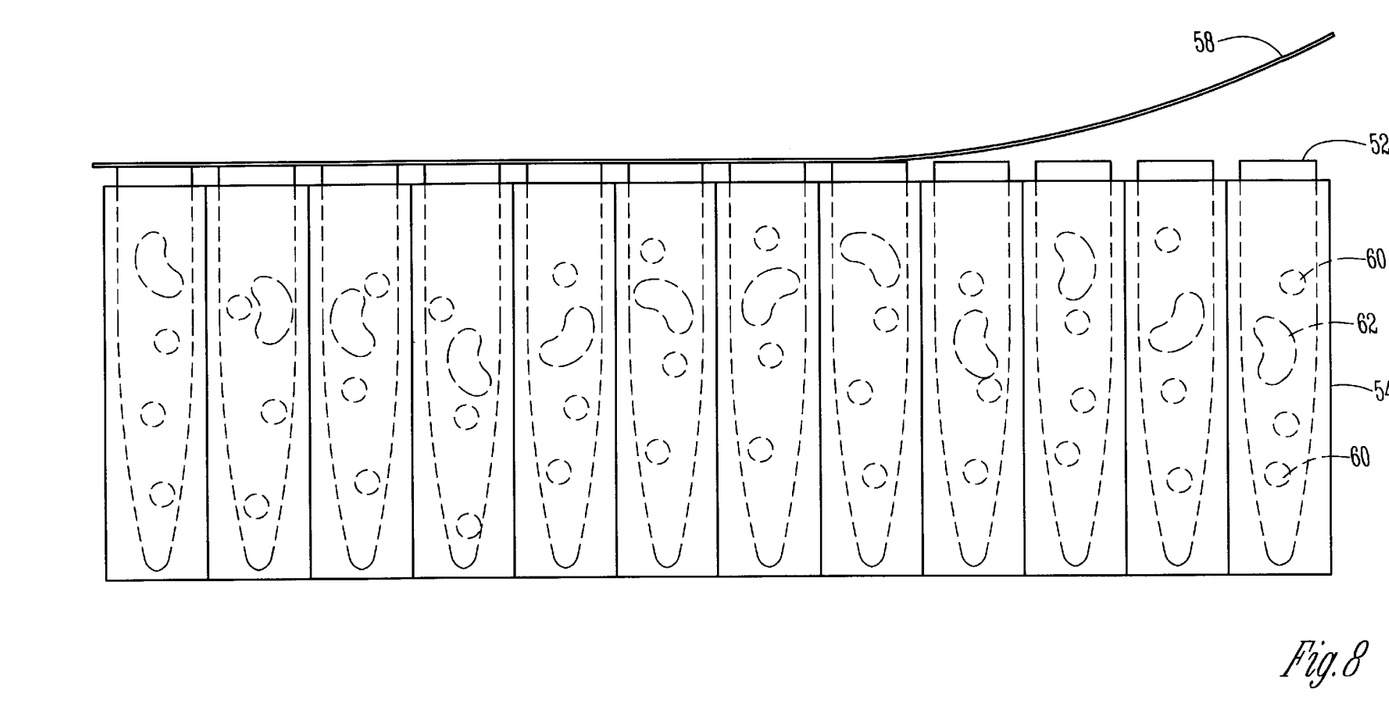
FIG. 8 is an enlarged view of another embodiment of the well plate holder and the well plates.

Before placing the well plate holder 54 into the holder 16, the tubes 52 may be sealed by a number of methods. FIG. 7 shows the tubes 52 and well plate holder 54 with a series of connected plastic lids 56 being inserted over the tubes 52. Alternatively, as shown in FIG. 8, a Mylar film 58 may be placed over the tubes 52 and sealed to the tubes 52 by heating the film 58.

Placed within each individual tube 52 is at least one agitation member 60. Preferably the agitation members 60 are comprised of 5/32 inch copper or stainless steel balls.

Stainless steel is preferred. Also placed in each individual tube 52 is a tissue sample 62, for example a bean or other plant tissue. The purpose of the agitation members 60 is to grind the sample 62 (discussed below).

A magnetic safety switch comprised of cover member 64 and housing member 66 is included as a safety device. The magnetic safety switch is conventional, and could take the form of a hall effect switch and a magnet. When the hinged cover 14 is in the closed position (FIGS. 2, 3, 5, 6), the magnetic safety switch allows the apparatus 10 to operate. When the hinged cover 14 is in the open position (FIG. 1), the cover member 64 is separated from the housing member 66 and the magnetic safety switch will not allow the apparatus 10 to operate. This way, the apparatus 10 will only operate when the hinged cover 14 is closed, protecting the user.

Figure 9:
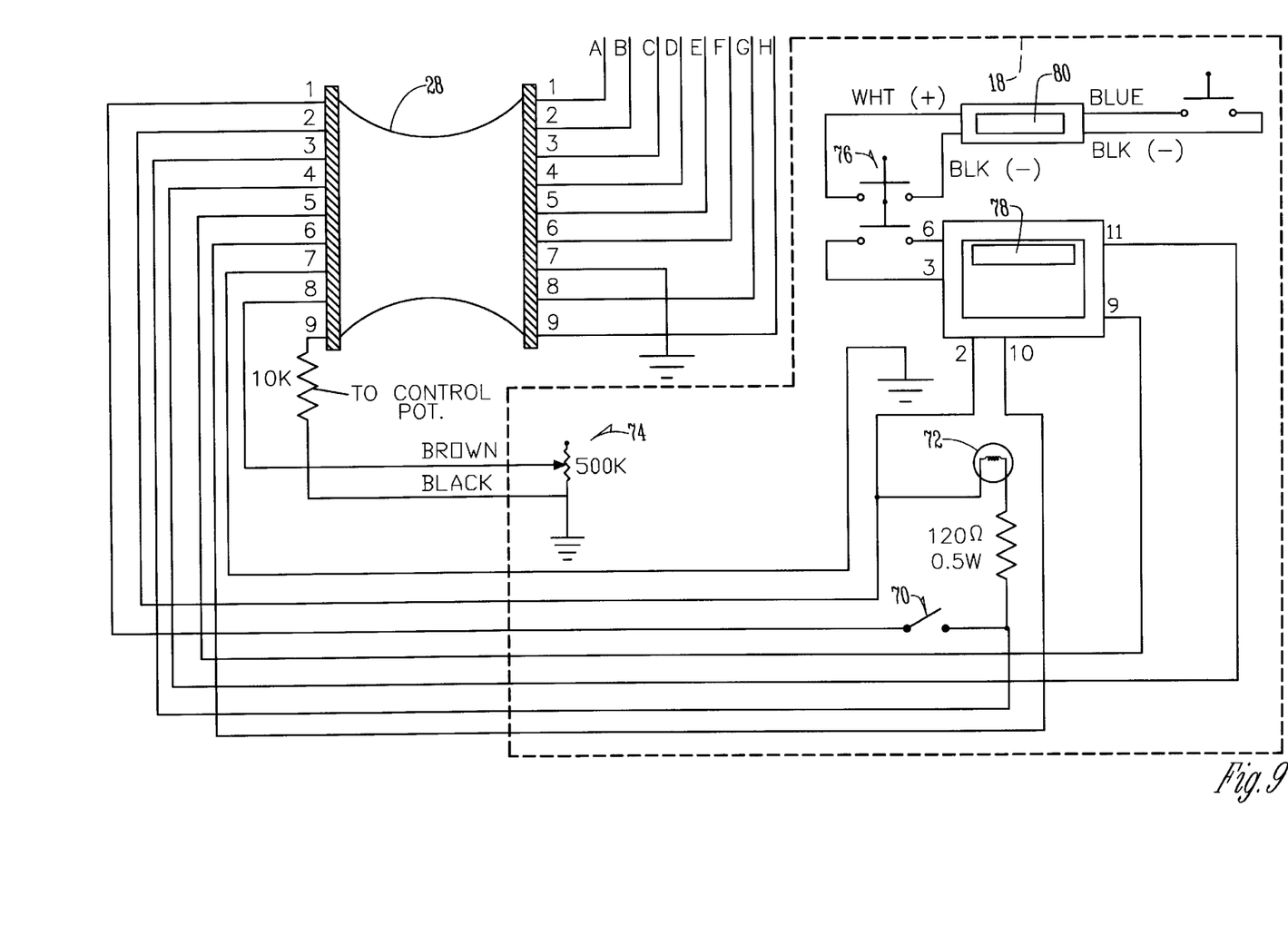
FIGS. 9–10 are electrical schematic diagrams of the present invention.
Figure 10:
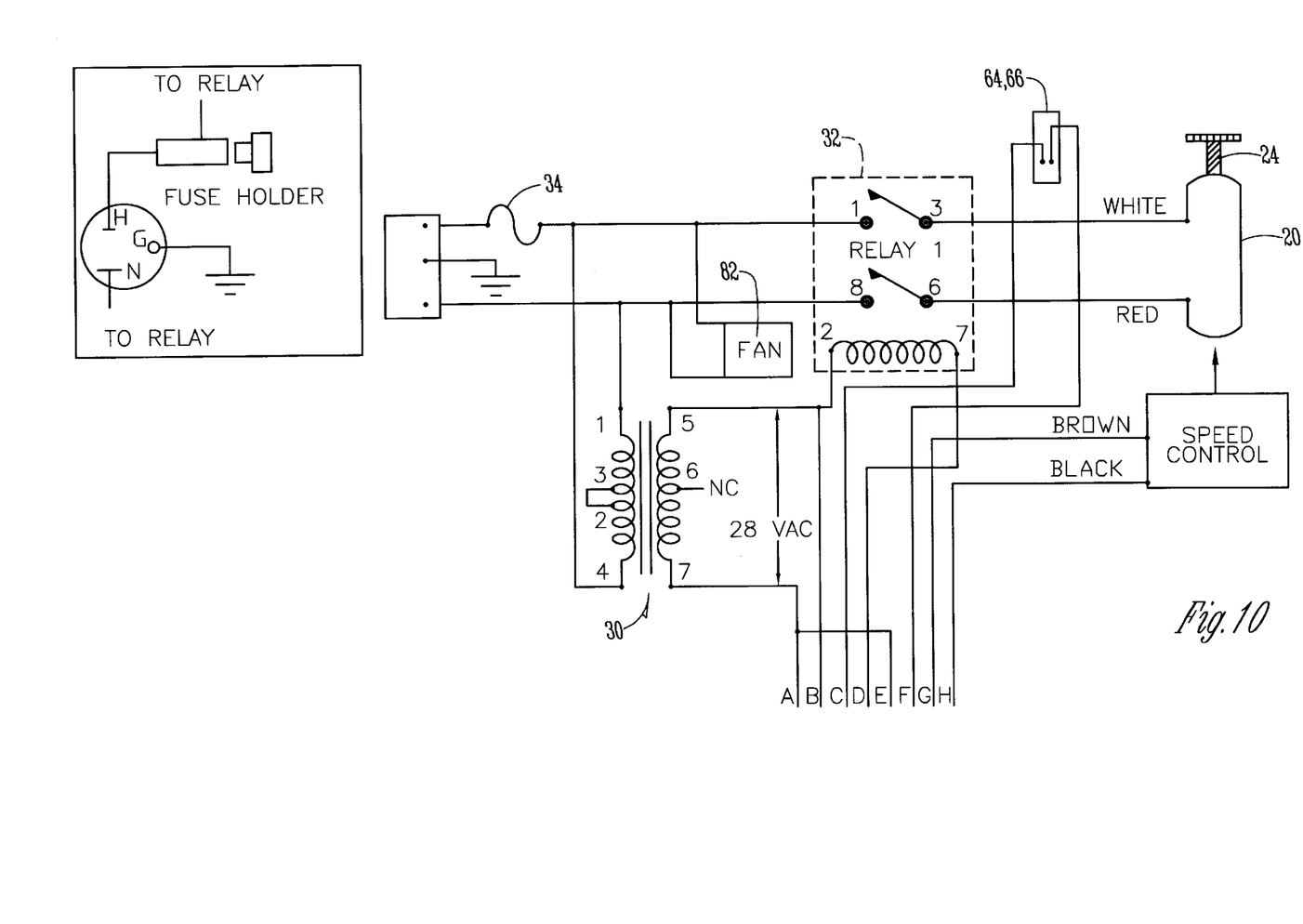

FIGS. 9 and 10 together show an electrical schematic diagram of the apparatus 10. The control panel 18 shown in FIGS. 1 and 2 is shown by the dashed line in FIG. 9. As shown in FIGS. 2 and 9, the control panel 18 includes a power switch 70 for turning on the power to the apparatus 10. A red lamp 72 indicates when the power is turned on. A speed control potentiometer 74 is used to control the speed of the apparatus 10. A switch 76 is used by the user to start a cycle. These components are connected to a time delay timer 78 and a cycle counter 80. The time delay timer is preferably comprised of a timer manufactured by Omron, part number H3CA. The circuit shown in FIGS. 9 and 10 shows the present invention for use with 115 VAC. Other designs are possible for use with 220 VAC, for example. FIG. 10 shows an optional cooling fan 82 which may be installed in the housing 12 to keep the interior of the housing 12 cool. For use in conjunction with the fan 82 or without the fan 82, one or more vents 68 may be formed in the walls of the housing 12 (FIG. 1).

The apparatus 10 of the present invention operates as follows. As an example, the operation of the apparatus 10 will be described for use in DNA extraction and analysis of seeds, but can be used for extraction of any cellular material or component, such as DNA, RNA, protein etc. Samples suitable for extraction according to the invention can include any plant or animal tissue.

First, the seeds to be used as samples 62 are placed in tubes in the well plates 52. In the case of seeds or other such hard coated materials, it may be desirable to soften the tissue by allowing the tissue to absorb liquid. For example, 300 uL of sterile water is placed in each tube to cover the sample 62. The sample 62 is soaked for two days, then the water is withdrawn using a multi pipette. Next, 400 uL PEX solution or other similar solution is added to each tube and soaked for thirty minutes. Next two agitation members 60 are added to each tube and sealed with plastic covers 56 or Mylar film 58. The well plate holder 54 is then placed in the holder 16 by sliding the well plate holder 54 into the end of the holder 16 between the upper and lower trays 48 and 42. The adjustment member 50 is then rotated clockwise to press the upper tray 48 down toward the lower tray 42 securing the well plate holder 54 in place. At this point, the samples ready to be ground by the apparatus 10.

To initiate the agitation, the user must first provide power to the apparatus 10 by closing the switch 70 on the control panel 18. The user can also select the speed of the apparatus 10 by rotating the knob connected to the speed control potentiometer 74. Typically, the saw 20 is allowed to run at 50–100% of its maximum rated speed for 30–90 seconds. By pressing the start cycle button 76, a cycle is started. When power is proved to the relay 32, power is supplied to the reciprocating saw 20. The saw 20 causes the holder 16 to move up and down with the reciprocating member 24. FIG. 5 shows the reciprocating motion of the holder 16 by showing two extreme positions (solid and dashed lines) of the holder 16. Since this agitating motion occurs at a high speed, the steel balls 60 will grind and homogenize the samples 62, preparing them for extraction and analysis.

After the agitation process, the well plate holder 54 is removed by rotating the adjustment member 50 counter clockwise and sliding the well plate holder 54 out of the holder 16. The remaining steps of DNA, protein, RNA or other cellular component extraction and analysis are not claimed as part of the present invention.

The preferred embodiment of the present invention has been set forth in the drawings and specification, and although specific terms are employed, these are used in a generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

What is claimed is:

1. An apparatus for the preparation of multiple tissue samples for the extraction of material therefrom comprising:
   a frame;
   a prime mover coupled to the frame, the prime mover having a reciprocating member for moving along a linear path with a reciprocating action relative to the frame;
   a plurality of elongated sample containers operatively coupled to the reciprocating member, each elongated sample container being oriented substantially parallel with the linear path in which the reciprocating member moves, each sample container being adapted to hold a tissue sample and at least one agitation member; and
   wherein the reciprocating action of the reciprocating member agitates the sample containers causing each agitation member to ground the tissue sample disposed within each respective sample container.

2. The apparatus of claim 1 wherein the agitation members are spherical.

3. The apparatus of claim 2 wherein the agitation members are comprised of ceramic balls.

4. The apparatus of claim 2 wherein the agitation members are comprised of metal balls.

5. The apparatus of claim 1 further comprising a control circuit electrically connected to the reciprocating saw for controlling the operation of the apparatus.

6. The apparatus of claim 3 wherein the control circuit further comprises a speed control circuit for controlling the speed of the reciprocating action.

7. The apparatus of claim 6 wherein the speed control circuit is adjustable by a user of the apparatus.

8. The apparatus of claim 5 wherein said control circuit further comprises a cycle counter.

9. The apparatus of claim 5 wherein the control circuit further comprises a timer for timing the operation of the apparatus.

10. The apparatus of claim 7 wherein the control circuit causes the reciprocating saw to operate for a certain length of time.

11. The apparatus of claim 5 wherein said control circuit further comprises a relay electrically connected to the prime mover for providing power to the prime mover when the relay is activated.

12. The apparatus of claim 1 further comprising a holder operatively coupled to the reciprocating member and attachable to the plurality of sample containers.

13. The apparatus of claim 1 further comprising a cover member adapted to enclose the plurality of sample containers while the apparatus is operating.

14. The apparatus of claim 13 further comprising a safety switch operatively coupled to the cover member and prime mover for disabling the operation of the apparatus when the cover member is not enclosing the plurality of sample containers.

15. The apparatus of claim 1 wherein the prime mover is comprised of a reciprocating saw.

16. The apparatus of claim 1 wherein the agitation members are comprised of $5/32$ inch spherical balls.

17. The apparatus of claim 1 further comprising a bushing rigidly coupled to the frame, wherein said reciprocating member passes through the bushing to stabilize the reciprocating member.

18. A method of preparing a plurality of tissue samples for material extraction comprising the steps of:
   providing a plurality of elongated sample containers;
   placing an agitation member and a tissue sample in each sample container;
   providing a motor having a reciprocating member which moves back and forth along a substantially linear path;
   coupling the plurality of sample containers to the reciprocating member, such that the sample containers are arranged parallel to the substantially linear path; and
   activating the motor in order to move the plurality of sample containers to cause the agitation members to ground the tissue samples.

19. The method of claim 18 further comprising the step of providing a control circuit for controlling the operation of the operation of the motor.

20. The method of claim 19 further comprising the step of controlling the speed of the motor.

21. The method of claim 16 further comprising the step of controlling the duration that the motor is activated.

22. The method of claim 19 further comprising the step of providing a cover to cover the plurality of sample containers.

23. The method of claim 22 further comprising the steps of:
   sensing whether the cover is covering the plurality of sample containers; and
   activating the motor only when it is sensed that the cover is covering the plurality of sample containers.

24. The method of claim 18 further comprising the step of providing a frame for supporting the motor in an upright position.

25. An apparatus for the preparation of multiple tissue samples for the extraction of material therefrom comprising:
   a prime mover having an elongated reciprocating member which moves back and forth along a linear path parallel to the length of the elongated reciprocating member;
   a sample holder coupled to the reciprocating member; and
   a plurality of elongated sample containers secured to the sample holder and disposed substantially parallel to the reciprocating member such that the sample containers reciprocate back and forth with the reciprocating member in a direction substantially parallel to the length of the sample containers.

26. The apparatus of claim 25 further comprising at least one agitation member disposed within each sample container.

27. The apparatus of claim 25 wherein the sample holder further comprises top and bottom plates for securing the sample containers between the top and bottom plates.

28. The apparatus of claim 27 further comprising a clamping member for biasing the top and bottom plates together to secure the sample containers between the top and bottom plates.

29. The apparatus of claim 25 wherein the sample holder further comprises a plurality of sample containers which are arranged parallel to each other and in a plurality of adjacent rows of sample containers.

* * * * *